United States Patent
Mikkaichi et al.

(10) Patent No.: US 8,758,375 B2
(45) Date of Patent: Jun. 24, 2014

(54) METHOD FOR SUTURING PERFORATION

(75) Inventors: Takayasu Mikkaichi, Tokyo (JP); Masayuki Iwasaka, Tokyo (JP)

(73) Assignee: Olympus Medical Systems Corp, Tokyo (JP)

( * ) Notice: Subject to any disclaimer, the term of this patent is extended or adjusted under 35 U.S.C. 154(b) by 780 days.

(21) Appl. No.: 11/238,016

(22) Filed: Sep. 28, 2005

(65) Prior Publication Data

US 2007/0073320 A1    Mar. 29, 2007

(51) Int. Cl.
*A61B 17/04*    (2006.01)

(52) U.S. Cl.
USPC ............ 606/153; 606/144; 606/142; 606/151; 606/232

(58) Field of Classification Search
USPC ......... 606/139, 144, 145, 148, 153, 167, 157; 600/113, 173, 104, 105
See application file for complete search history.

(56) References Cited

U.S. PATENT DOCUMENTS

| | | | |
|---|---|---|---|
| 4,235,238 A | 11/1980 | Ogiu et al. | |
| 5,297,536 A | 3/1994 | Wilk | |
| 5,395,319 A | 3/1995 | Hirsch et al. | |
| 5,445,167 A | 8/1995 | Yoon et al. | |
| 5,458,131 A * | 10/1995 | Wilk | 600/105 |
| 5,507,754 A | 4/1996 | Green et al. | |
| 5,810,848 A | 9/1998 | Hayhurst | |
| 5,817,108 A | 10/1998 | Poncet | |
| 5,824,009 A | 10/1998 | Fukuda et al. | |
| 5,948,002 A | 9/1999 | Bonutti | |
| 6,024,747 A * | 2/2000 | Kontos | 606/144 |
| 6,066,090 A * | 5/2000 | Yoon | 600/113 |
| 6,066,146 A | 5/2000 | Carroll et al. | |
| 6,086,596 A | 7/2000 | Durham | |
| 6,203,554 B1 | 3/2001 | Roberts | |
| 6,352,503 B1 | 3/2002 | Matsui et al. | |
| 6,491,707 B2 * | 12/2002 | Makower et al. | 606/157 |
| 6,500,184 B1 | 12/2002 | Chan et al. | |
| 6,535,764 B2 | 3/2003 | Imran et al. | |
| 6,572,626 B1 | 6/2003 | Knodel et al. | |

(Continued)

FOREIGN PATENT DOCUMENTS

| | | |
|---|---|---|
| JP | 07-328020 A | 12/1995 |
| JP | 3032847 | 1/1997 |

(Continued)

OTHER PUBLICATIONS

U.S. Office Action dated Aug. 27, 2013 from related U.S. Appl. No. 12/057,604.

(Continued)

*Primary Examiner* — Vy Q Bui

(74) *Attorney, Agent, or Firm* — Scully, Scott, Murphy & Presser, P.C.

(57) ABSTRACT

A method for suturing a perforation comprises the steps of: observing an area around the perforation from an inside of a hollow organ by an observation device inserted from a natural opening of a living body; observing the area around the perforation from a body cavity side of the hollow organ by an observation device inserted from the natural opening of the living body; thrusting a needle of a suture unit inserted from the natural opening of the living body into a tissue around the perforation of the hollow organ to make a suture thread puncture the tissue via the needle; and closing the perforation by tightening up the suture thread puncturing the tissue.

7 Claims, 23 Drawing Sheets

(56) References Cited

U.S. PATENT DOCUMENTS

| | | |
|---|---|---|
| 6,719,765 B2 | 4/2004 | Bonutti |
| 6,840,899 B2 | 1/2005 | Koga et al. |
| 7,621,925 B2 | 11/2009 | Saadat et al. |
| 7,651,509 B2 | 1/2010 | Bojarski et al. |
| 8,128,640 B2 | 3/2012 | Harris et al. |
| 2001/0049497 A1 | 12/2001 | Kalloo et al. |
| 2002/0055757 A1 | 5/2002 | Torre et al. |
| 2003/0055442 A1 | 3/2003 | Laufer et al. |
| 2003/0105474 A1 | 6/2003 | Bonutti |
| 2003/0130694 A1 | 7/2003 | Bojarski et al. |
| 2003/0163160 A1 | 8/2003 | O'Malley et al. |
| 2003/0216613 A1 | 11/2003 | Suzuki et al. |
| 2003/0236535 A1 | 12/2003 | Onuki |
| 2004/0167548 A1 | 8/2004 | Bonutti |
| 2004/0249395 A1 | 12/2004 | Mikkaichi et al. |
| 2005/0033363 A1 | 2/2005 | Bojarski et al. |
| 2005/0059984 A1 | 3/2005 | Chanduszko et al. |
| 2006/0178680 A1 | 8/2006 | Nelson et al. |
| 2007/0021714 A1 | 1/2007 | Miller |
| 2007/0027476 A1 | 2/2007 | Harris et al. |
| 2007/0032796 A1 | 2/2007 | Chin-Chen et al. |
| 2007/0049970 A1 | 3/2007 | Belef et al. |

FOREIGN PATENT DOCUMENTS

| | | |
|---|---|---|
| JP | 10-504222 | 4/1998 |
| JP | 2000-516513 | 12/2000 |
| JP | 2002-233530 | 8/2002 |
| JP | 2004-601 | 1/2004 |
| JP | 2004-358045 | 12/2004 |
| JP | 2005-211690 | 8/2005 |
| WO | 99/21490 A1 | 5/1999 |
| WO | 2005/065412 A2 | 7/2005 |
| WO | 2005/079673 A2 | 9/2005 |

OTHER PUBLICATIONS

U.S. Office Action dated Nov. 10, 2010, received in related U.S. Appl. No. 12/057,971.

European Search Report dated Mar. 14, 2013 from corresponding European Application No. 06 810 782.0.

European Search Report dated Jun. 26, 2013 from corresponding European Application No. 06 81 0746.5.

U.S. Office Action dated Jun. 12, 2013 received in related U.S. Appl. No. 12/057,971.

English language abstract of WO 99/21490 A1 published May 6, 1999.

U.S. Office Action dated Nov. 5, 2012, received in related U.S. Appl. No. 12/057,604.

* cited by examiner

METHOD FOR SUTURING PERFORATION

BACKGROUND OF THE INVENTION

1. Field of the Invention

The present invention relates to a method for suturing by inserting a suture instrument via the mouth or the anus. For example, the present invention relates to a method of suturing a perforation formed in a wall of a hollow organ.

2. Description of Related Art

In the case of performing treatment in a body of a patient, the treatment can be performed by incising the body of the patient by surgical operation, or by oral endoscopic treatment or transanal endoscopic treatment. A method for suturing a perforation formed in an abdominal area by surgical operation is disclosed in FIGS. 6a to 6c of U.S. Pat. No. 6,066,146. According to this suturing method, a needle is thrust into the tissue around the perforation, and an anchor equipped with a suture thread is then extruded from the needle. After the needle is drawn out from the tissue, two suture threads across the perforation are knotted together to close the perforation.

The treatment using an endoscope is carried out by passing a forceps, high-frequency treatment instrument, incision instrument, suture instrument or the like through a channel of the endoscope. When the medical treatment is carried out by using an endoscope inserted into a lumen through a natural opening of a living body such as the mouth, anus, or the like, for example, a hole is formed by removing the tissue from the abdominal cavity or incising the tissue in the abdominal cavity, and the medical treatment is then carried out by approaching the abdominal cavity through this hole from the inside of the lumen. After performing the medical treatment, the formed hole is sutured by a suture instrument.

A method for suturing in a hollow organ is disclosed in FIGS. 6 to 9 of Japanese Laid-Open Patent Application No. 2004-601, for example. According to this suturing method, the tissue is drawn into an overtube, and a needle is then thrust through this tissue from the proximal side to the distal side thereof. From the inside of the needle, an anchor equipped with a suture thread is pushed out to the distal side of the tissue. After that, the needle is pulled out, and thereby the suture thread penetrates through the tissue and tightens up the tissue. There is also a method disclosed in FIG. 1, FIG. 4, FIGS. 5A to 5C of U.S. Pat. No. 5,297,536. According to this method, a flexible endoscope is inserted into the vicinity of a perforation via the mouth or the anus. The tissue around the perforation is aspirated by a tube of the flexible endoscope. When an O-ring provided at the outside of the tube is pushed out from the tip of the tube, the aspirated tissue is clamped by the O-ring.

SUMMARY OF THE INVENTION

A method for suturing a perforation of the present invention comprises the steps of: observing an area around the perforation from an inside of a hollow organ by an observation device inserted from a natural opening of a living body; observing the area around the perforation from a body cavity side of the hollow organ by an observation device inserted from the natural opening of the living body; thrusting a needle of a suture unit inserted from the natural opening of the living body into a tissue around the perforation of the hollow organ to make a suture thread puncture the tissue via the needle; and closing the perforation by tightening up the suture thread puncturing the tissue.

DETAILED DESCRIPTION OF THE INVENTION

First Embodiment

Figure 1:
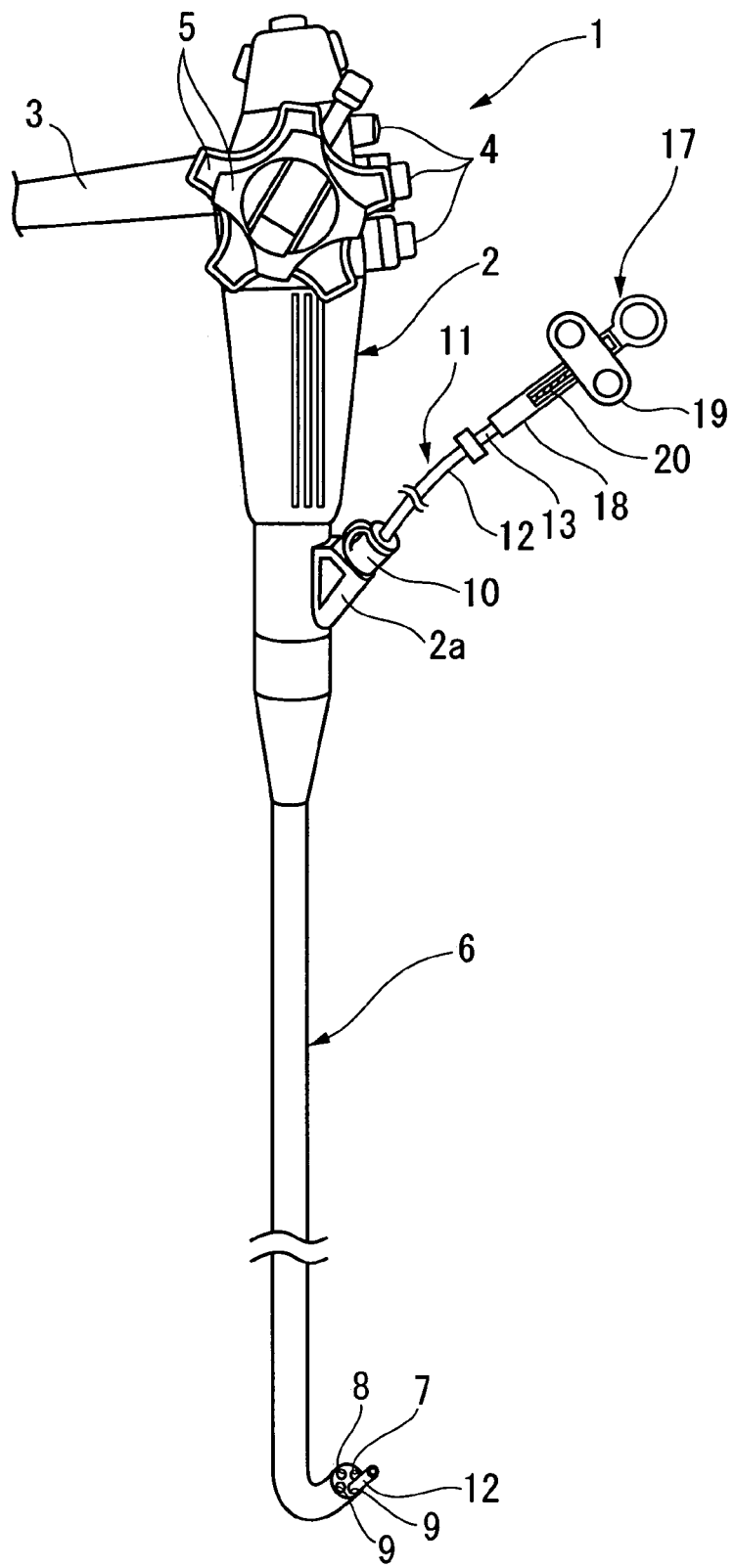
FIG. 1 is a view showing a schematic constitution of an endoscope and a suture unit.

In FIG. 1, an endoscope and a suture unit used in this embodiment are shown. An endoscope 1 (flexible endoscope) has an endoscope operation unit 2 which is operated by an operator. The endoscope operation unit 2 is connected to a control device via a universal cable 3 and equipped with various switches 4 and angle knobs 5. At the tip of the endoscope operation unit 2, an endoscope insertion part 6 that is flexible and long is extendedly formed. At the tip of the endoscope insertion part 6, an observation device (first observation device, hereinafter, merely referred to as observation device) 7 for an endoscope which obtains an image of the internal body, a lighting unit 8, and a tip opening of a channel 9 are provided. As the observation device 7, an imaging device having a CCD (Charge Coupled Device) or an optical fiber can be used. The lighting unit 8 has an optical fiber that conducts light from a light source. The channel 9 opens at a lateral part 2a of the endoscope operation unit 2 through the endoscope insertion part 6. At an opening of the lateral part 2a, a cap 10 is provided. In the cap 10, an insertion hole is formed, and a treatment tool such as a suture unit 11 or the observation device is inserted into the channel 9 through this insertion hole.

Figure 2:
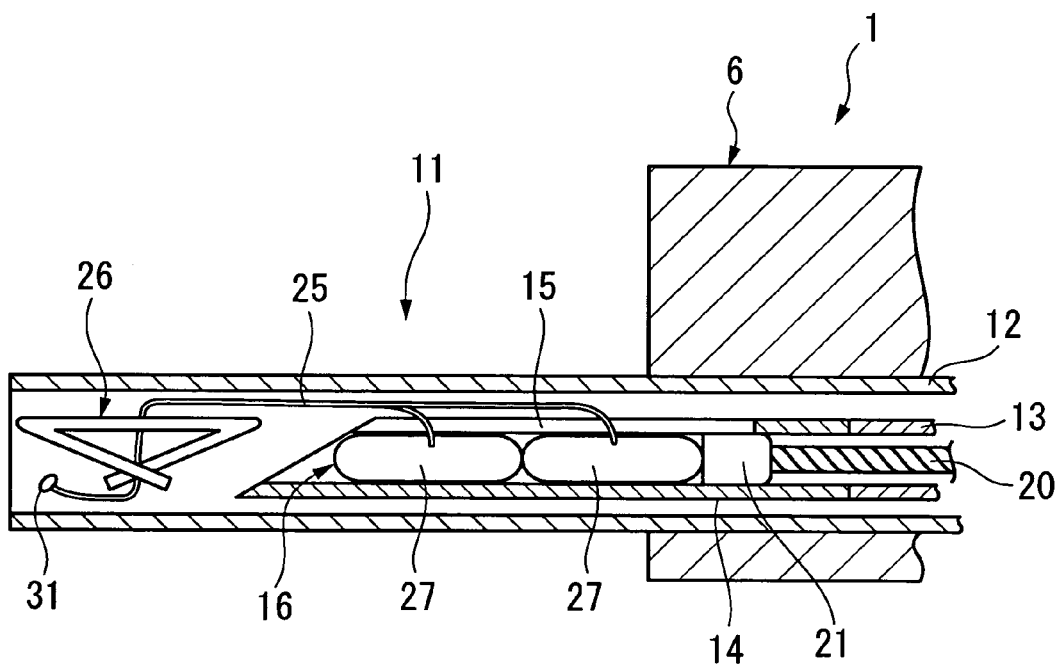
FIG. 2 is a cross-sectional view of a suture unit and an end portion of an endoscope.
Figure 3:
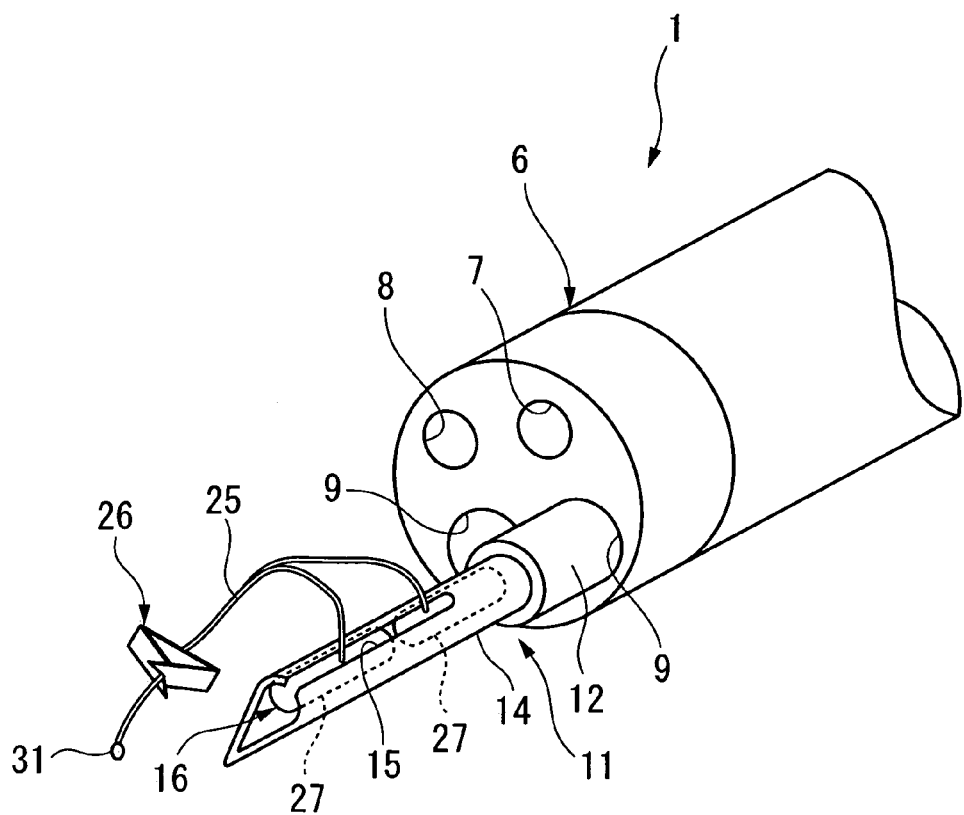
FIG. 3 is a perspective view of a suture unit and an end portion of an endoscope.

As shown in FIGS. 1 to 3, in the suture unit 11, a flexible inner sheath 13 is passed through the inside of a flexible outer sheath 12 so as to be able to freely move forward or backward. To the tip of the inner sheath 13, a needle 14 is fixed. The needle 14 has a slit 15 formed in a longitudinal direction from the tip thereof. A suture instrument 16 is contained inside of the needle 14. Each of the lengths of the outer sheath 12 and the inner sheath 13 is longer than that of the channel 9 of the endoscope 1. At a proximal end of the inner sheath 13, an operation unit 17 is provided. The operation unit 17 has a handle 19 which can freely slide with respect to a main body 18 of the operation unit. To the handle 19, a proximal end of a pusher 20 is fixed. The pusher 20 extends through the inside of the inner sheath 13 to the inside of the needle 14. A distal end portion 21 of the pusher 20 is pressed against the suture instrument 16.

Figure 4:
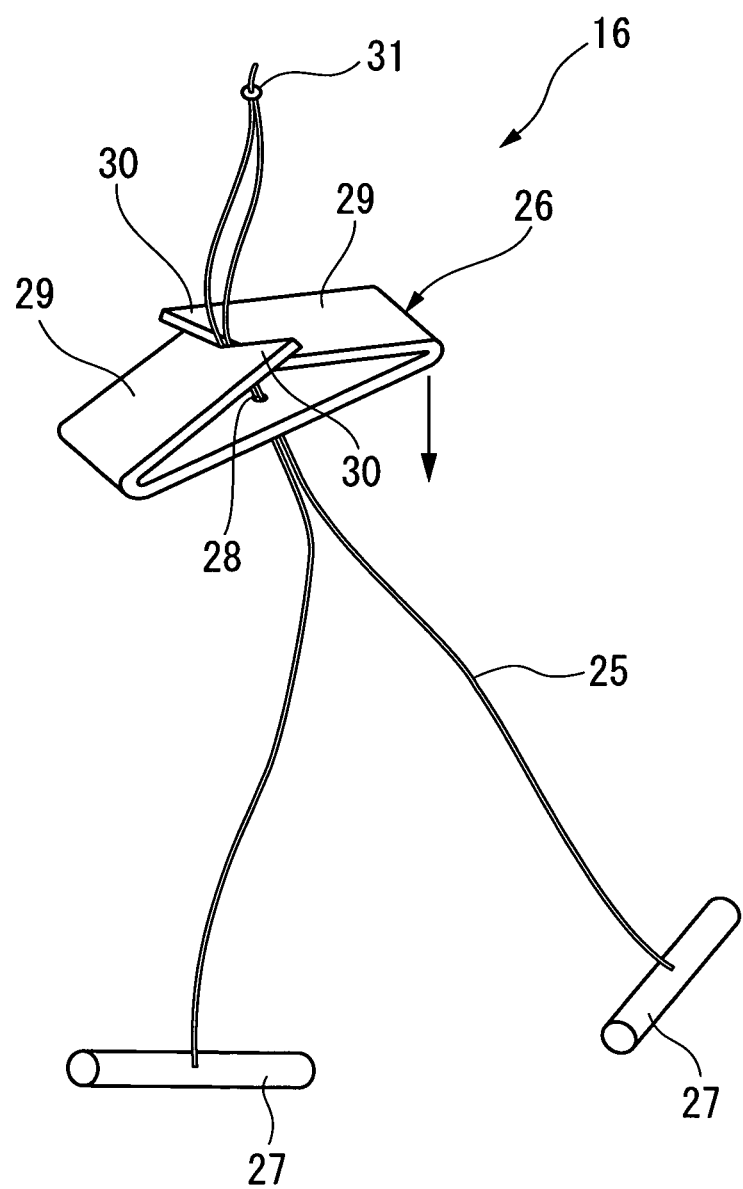
FIG. 4 is a view showing a constitution of a suture instrument.

As shown in FIG. 4, the suture instrument 16 has a suture thread 25. The suture thread 25 is folded approximately in two and a knot 31 is formed in the vicinity of its turn-around point. Moreover, the suture thread 25 is bundled at both end portions thereof and passed through a stopper 26 that is substantially triangular. To each end portion of the suture thread 25, an anchor 27 is fixed. The anchor 27 has a cylindrical shape and the suture thread 25 is fixed at an approximately center portion in a longitudinal direction of the anchor 27. The stopper 26 includes a long, thin plate member in which a hole 28 is formed at the center portion in a longitudinal direction thereof, through which the suture thread 25 is passed. Both end portions 29 in a longitudinal direction of the stopper 26 are diagonally folded back to hold the suture thread 25 therebetween. Both end portions 29 in a longitudinal direction of the stopper 26 are cut to form triangular sections 30. Both end portions 29 of the stopper 26 are diagonally folded back so that the sections 30 intersect with each other to hold the suture thread 25 therebetween. As a result, the suture thread 25 is prevented from passing through a space formed between end portions 29. When the knot 31 of the suture thread 25 is pulled in a direction away from the stopper 26, both end portions 29 of the stopper 26 are slightly opened. Accordingly, the stopper 26 allows the suture thread 25 to move in the same direction. On the other hand, when end portions of the suture thread 25 at the side of the anchors 27 are pulled, the suture thread 25 is ready to move in a direction shown by an arrow in FIG. 4. However, both end portions 29 of the stopper 26 close and secure the suture thread 25 at this time, and thereby the suture thread 25 does not move.

As shown in FIG. 3, the suture instrument 16 sequentially holds two anchors 27 in an inner hole of the needle 14. The suture thread 25 is drawn out from the slit 15 of the needle 14. As shown in FIG. 2, the stopper 26 is held at a more distal end portion than the needle 14 in the outer sheath 12. The number of the anchors 27 and the shape of the stopper 26 are not limited to the embodiment shown in the figures.

Next, a suturing method of this embodiment will be explained mainly with reference to FIGS. 5 to 12. FIGS. 5 to 12 are pattern diagrams illustrating manipulation and show the stomach as an example of a hollow organ.

Figure 5:
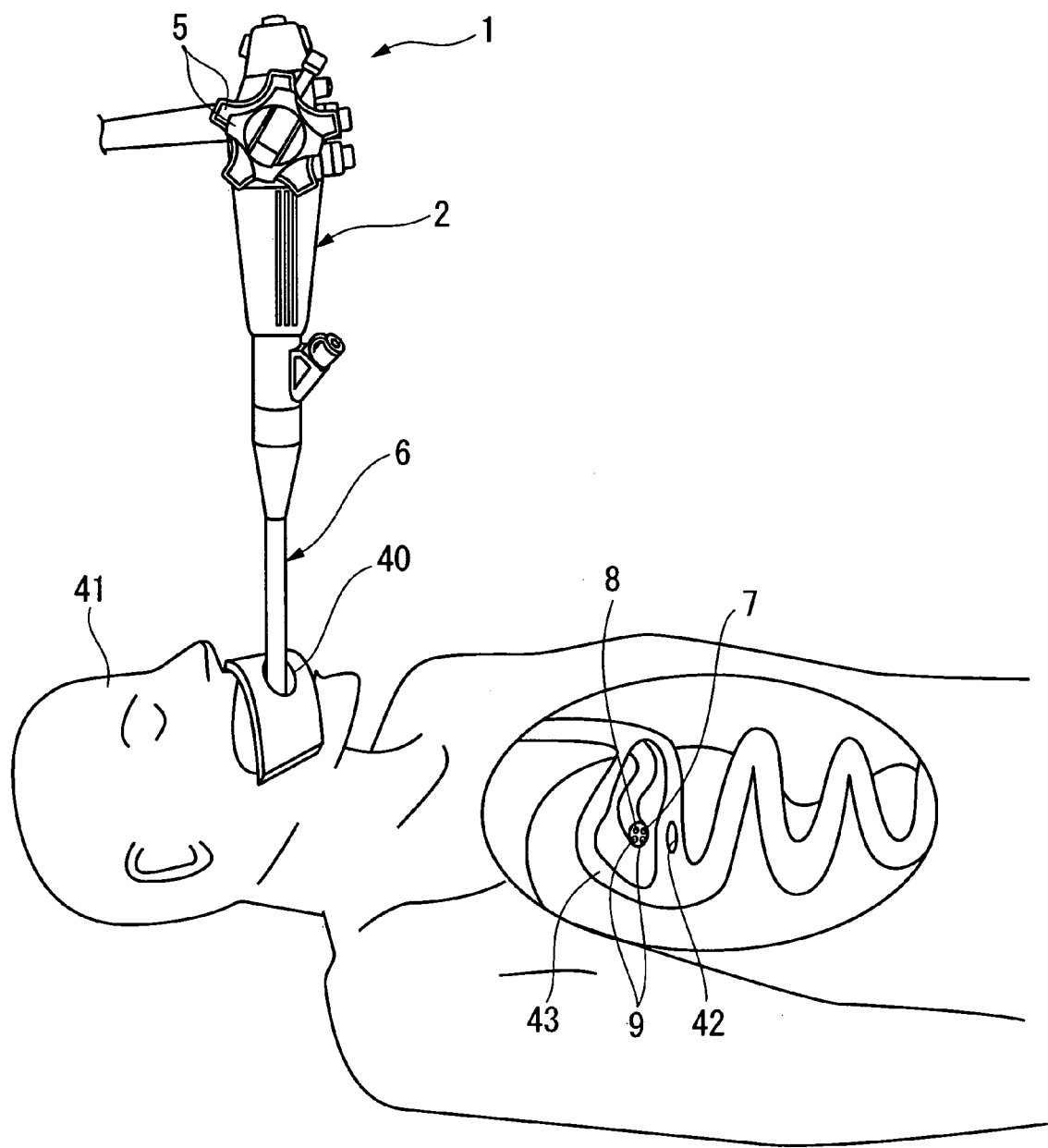
FIG. 5 is a schematic view showing a step of inserting an endoscope into the stomach of a patient to observe a perforation from the inside of the stomach.
Figure 6:
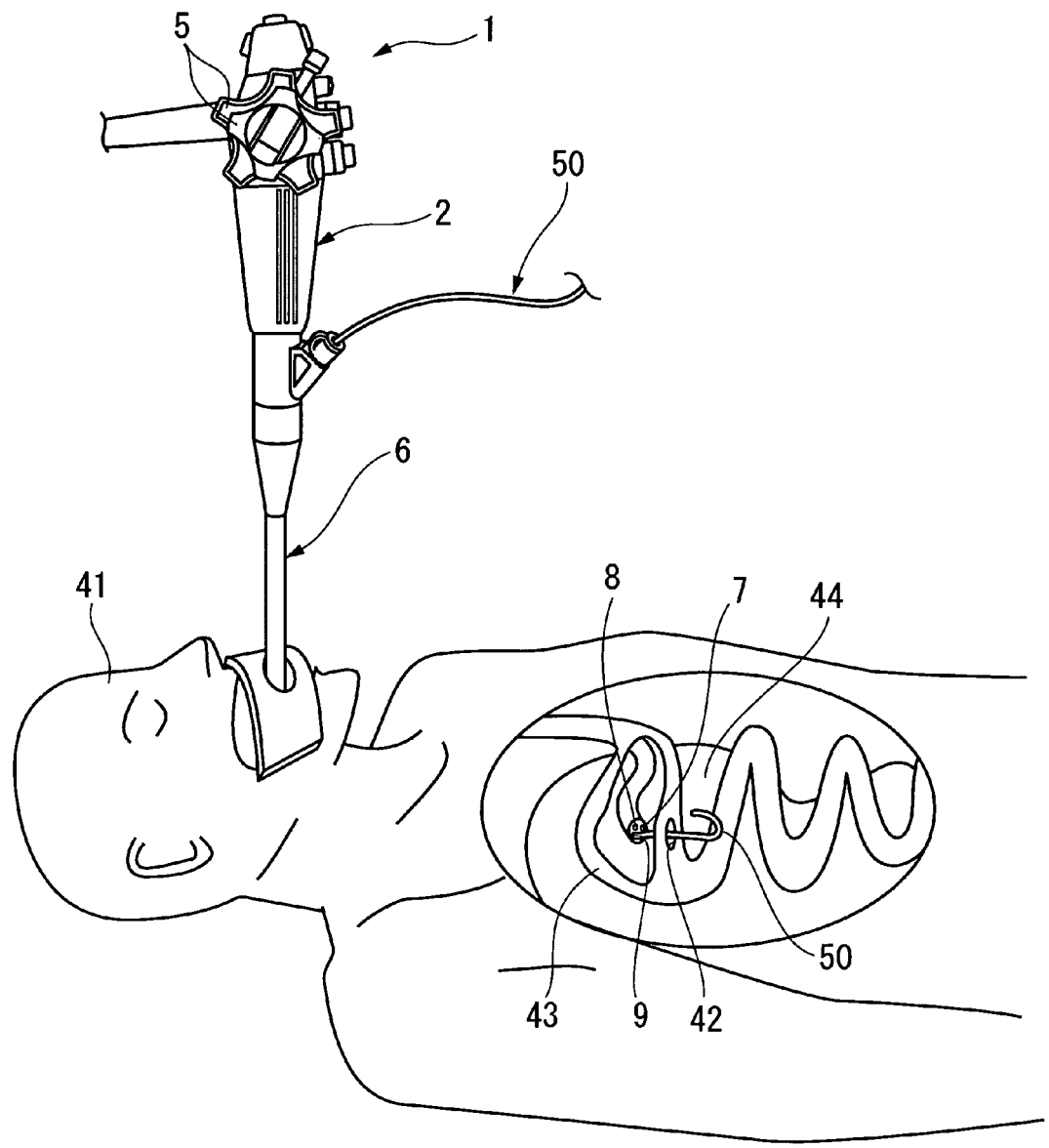
FIG. 6 is a schematic view showing a step of observing the outside of the stomach.

As shown in FIG. 5, the endoscope insertion part 6 is inserted from the mouth (a natural opening of a living body, such as the anus, nose, or ear) of a patient 41 prepared with a mouthpiece 40. When the tip of the endoscope insertion part 6 is bent by the angle knob 5, a perforation 42 can be checked by the observation device 7 from the inside of the stomach 43 (the inside of the hollow organ). As shown in FIG. 6, an observation device (second observation device) 50 is passed through the channel 9 of the endoscope 1. The observation device 50 is, for example, a catheter having a camera at the tip thereof. The observation device 50 may be a long and narrow fiberscope.

The tip of the observation device 50 is inserted from the perforation 42 into the abdominal cavity 44, and the tip of the observation device 50 is then bent back by a wire or the like, which is not shown in the figures. By using the observation device 50, an area around the perforation 42 to be punctured with the needle 14 (referred also to as a puncture position or a position through which the needle 14 passes) is observed from an abdominal cavity 44 side (which is also the side at which the anchor 27 is placed), that is, from the outside of the stomach 43 (referred also as a body cavity side of the hollow organ or the abdominal cavity side) to check that other tissues such as the small intestine, the liver, or the like do not exist at the position through which the needle 14 is passed in order to prevent these tissues from being punctured or sutured together.

Figure 7:
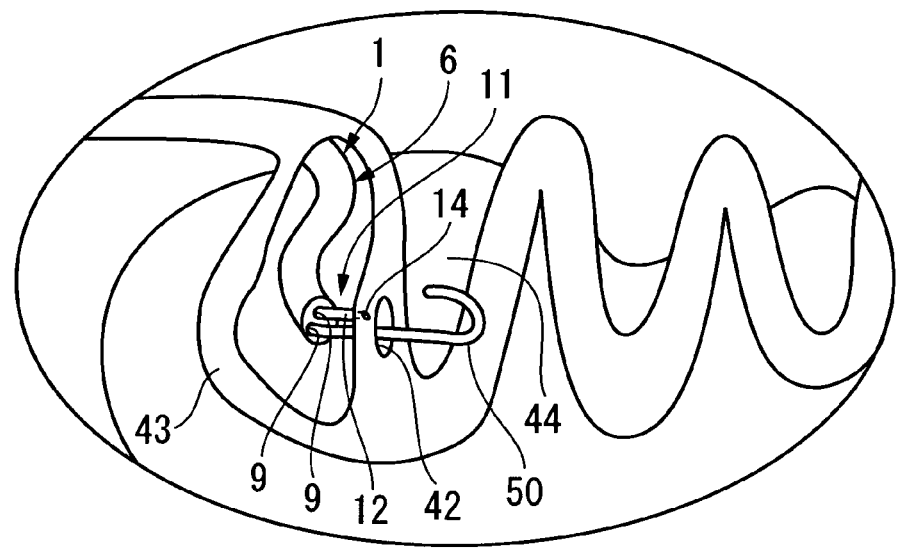
FIG. 7 is a schematic view showing a step of puncturing the tissue with a needle of a suture unit.
Figure 8:
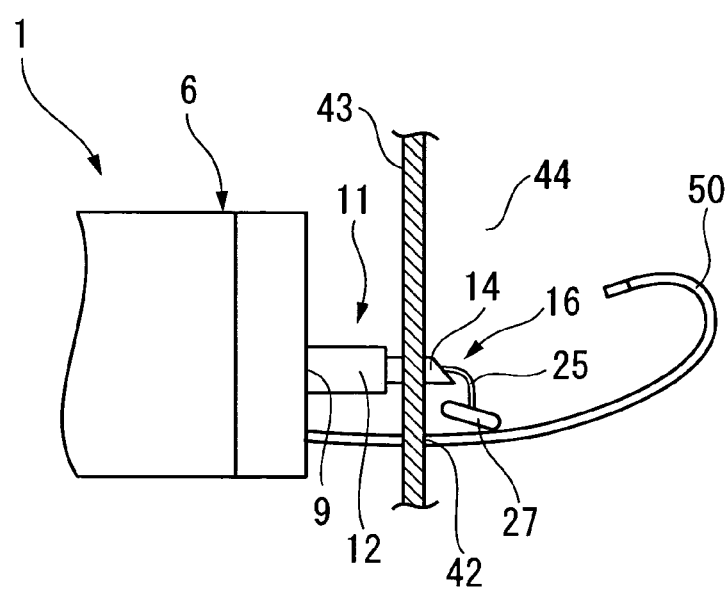
FIG. 8 is a schematic view showing a step of putting an anchor out from a needle to the outside of the stomach.

As shown in FIG. 7, the suture unit 11 is projected to puncture the tissue around the perforation 42 with the needle 14 while observing the stomach 43 from the abdominal cavity 44 side by the observation device 50. When the tissue is punctured, the needle 14 is projected from the outer sheath 12 as shown in FIG. 3. The stopper 26 which is contained at the more distal end portion than the needle 14 is extruded from the outer sheath 12 into the stomach 43 when projecting the needle 14. When the needle 14 is moved forward with the outer sheath 12 fixed, the needle 14 punctures the tissue. When the handle 19 provided at an operator-side as shown in FIG. 1 is pushed in, the pusher 20 moves forward, and the first anchor 27 is pushed out from the tip of the needle 14 into the abdominal cavity 44, as shown in FIG. 8. When the first anchor 27 is pushed out, the pusher 20 is stopped, and the needle 14 is drawn out from the tissue. The first anchor 27 remains on the abdominal cavity 44 side. The suture thread 25 penetrates through the tissue. The stopper 26 is then in the stomach 43.

Figure 9:
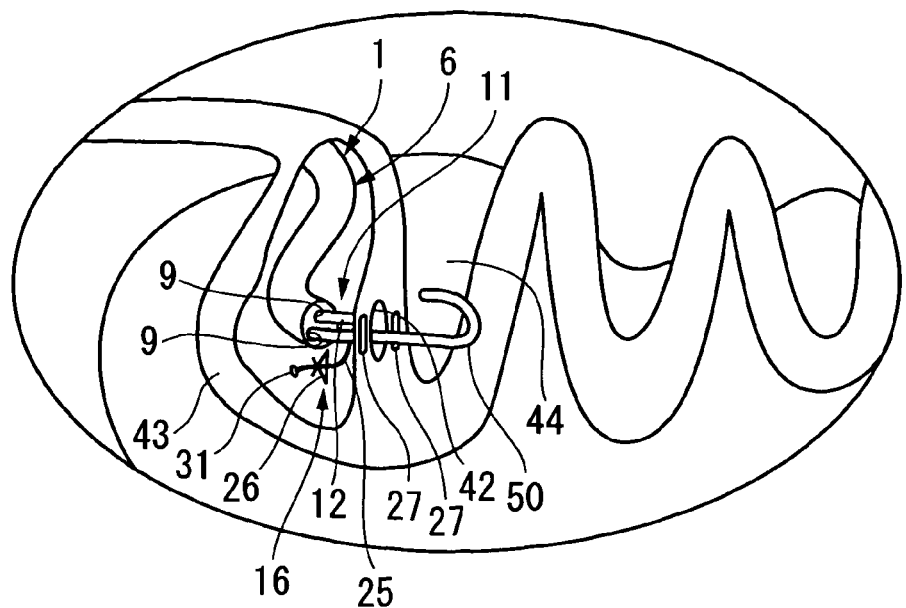
FIG. 9 is a schematic view in which two anchors are placed outside the stomach.

Moreover, the needle 14 is thrust again at an approximately symmetrical position with respect to the position at which the needle 14 is previously thrust centered about the perforation. In the same manner as when using the first anchor 27, when the needle 14 penetrates through the tissue, the pusher 20 is moved forward. The second anchor 27 is pushed out into the abdominal cavity 44. As shown in FIG. 9, when the needle 14 is drawn back, the second anchor 27 remains on the abdominal cavity 44 side, the suture thread 25 penetrates through the tissue, and two anchors 27 are placed on the abdominal cavity 44 side to sandwich the perforation 42 therebetween.

Figure 10:
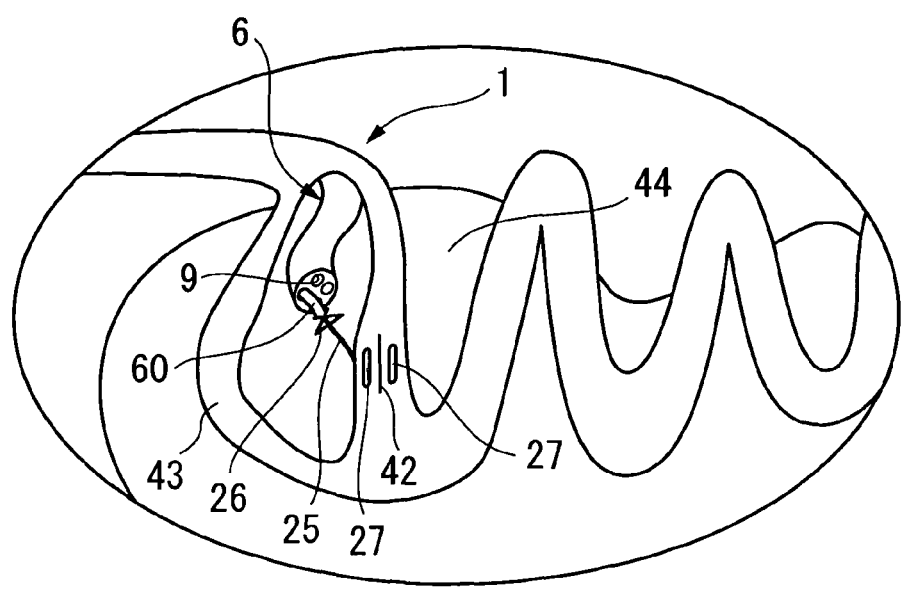
FIG. 10 is a schematic view showing a step of tightening up a perforation by a suture instrument.

Next, as shown in FIG. 10, after the observation device 50 is drawn back to the inside of the stomach 43, the suture thread 25 is pulled so that the anchor 27 and the stopper 26 tighten up the tissue, and thereby the perforation 42 is sutured. When the suture thread 25 is pulled, a forceps 60 shown in FIG. 11, for example, is used. The forceps 60 is passed through the channel 9 in the place of the observation device 50. The forceps 60 has an outer sheath 61 having an external diameter larger than the anchor 27 and an inner sheath 62 passed through the outer sheath 61 so as to freely move forward or backward. At the tip of the inner sheath 62, a supporting member 63 is provided, and a pair of grip segments 64 are supported on the supporting member 63 so as to freely open or close.

Figure 12:
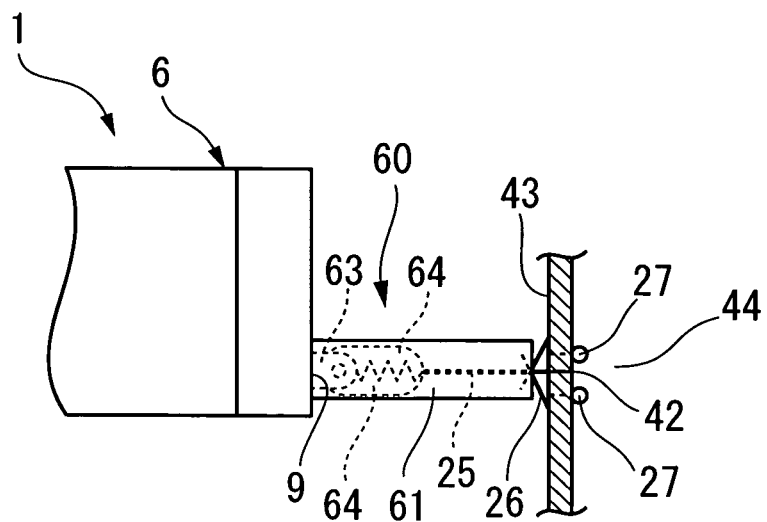
FIG. 12 is a view in which a perforation is sutured by a forceps and a suture instrument.

After the knot 31 of the suture thread 25 of the suture instrument 16 is gripped by the grip segments 64, the outer sheath 61 is moved forward to press the tip of the outer sheath 61 against the stopper 26. As shown in FIG. 12, when the outer sheath 61 moves further forward, the stopper 26 is pushed into the wall of the stomach 43. Since the stopper 26 is constructed to be able to move in this direction, the stopper 26 moves toward the wall. Since the position of the pair of the grip segments 64 does not change, the stopper 26 moves relatively forward with respect to the suture thread 25. As a result, the distance between the stopper 26 and the anchor 27 decreases. This pulls together the tissue around the perforation 42, and the perforation 42 is sutured by the suture thread 25. After suturing the perforation 42 by the suture instrument 16, the outer sheath 61 is moved backward, and the grip segments 64 are then opened to release the suture thread 25. Although the tip of the stopper 26 can move in a direction in which the tissue is tightened up by the suture thread 25, it acts to tighten up the suture thread 25 in a direction for loosening the suture thread 25. As a result, the suture thread 25 is not loosened, even if the suture instrument 16 is placed inside of the stomach 43.

Figure 13:
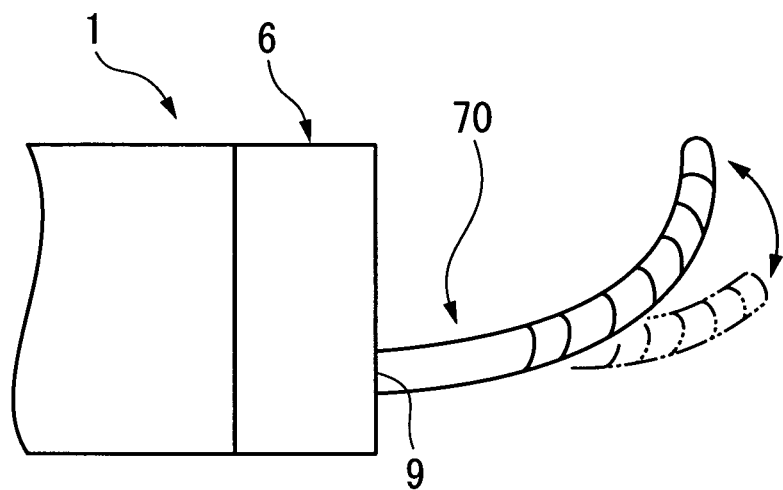
FIG. 13 is a schematic view showing a rod which is an example of a retracting instrument.
Figure 14:
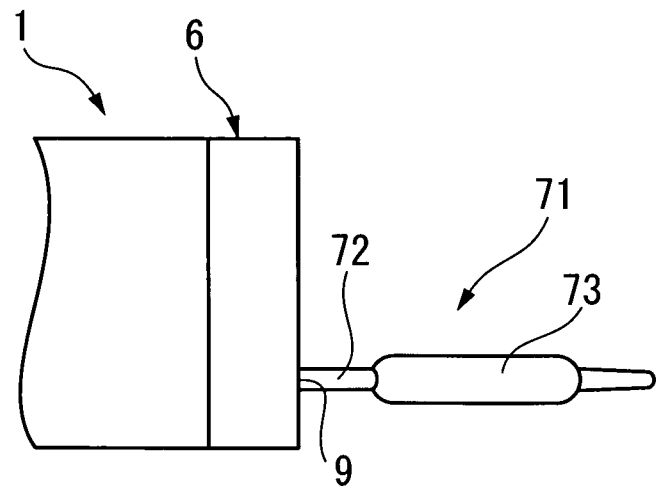
FIG. 14 is a schematic view showing a balloon catheter which is an example of a retracting instrument.
Figure 15:
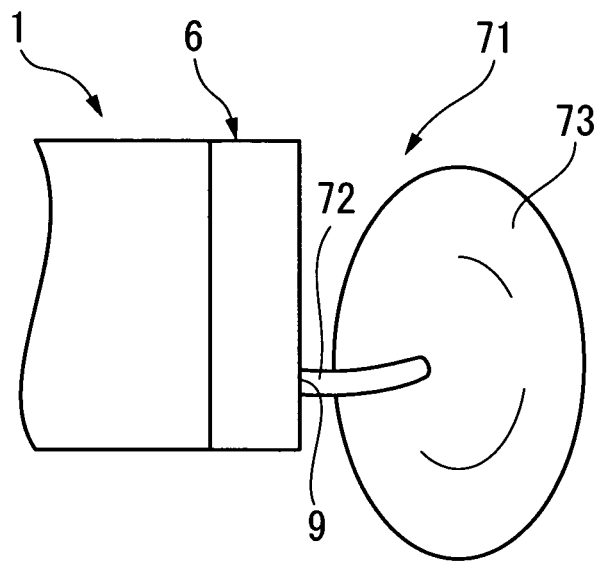
FIG. 15 is a schematic view showing a balloon catheter in which a balloon is inflated.
Figure 16:
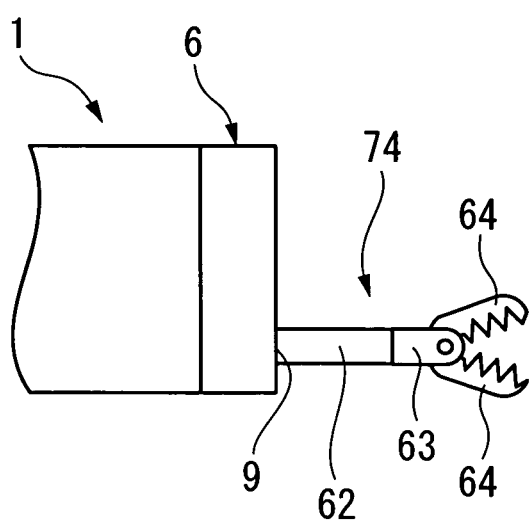
FIG. 16 is a schematic view showing a forceps which is an example of a retracting instrument.

When a hollow organ such as the small intestine or the colon or another organ such as the spleen or the liver (hereinafter, merely referred to as tissue) exists in the area around the perforation 42 (the position through which the needle 14 is passed), the other tissue is pulled away from the stomach 43 by inserting a retracting instrument. The retracting instrument used in this case is exemplified in FIGS. 13 to 16. A retracting instrument shown in FIG. 13 is a rod 70 of which a tip portion can be bent. When the rod 70 is bent, the other hollow organ is pushed off to form a space through which the needle 14 is passed. A retracting instrument shown in FIGS. 14 and 15 is a balloon catheter 71. When a balloon 73 provided at the tip portion of a catheter 72 is inflated by supplying a fluid from the operator-side to push off the other hollow organ, the space through which the needle 14 is passed is formed. A retracting instrument shown in FIG. 16 is a forceps 74. When the other hollow organ is grasped by the forceps 74 to draw it away from the stomach 43, the space through which the needle 14 is passed is formed. At the tip portions of these retracting instruments, an optical fiber or an observation device having a CCD may be provided. When the observation device is provided, it becomes possible to retract other tissues while observing the state of the abdominal cavity 44.

In this embodiment, the perforation 42 is observed from the inside of the stomach 43 by the observation device 7 of the endoscope 1 at first, and the perforation 42 is then observed from the abdominal cavity 44 side by the observation device 50. After that, the suture unit 11 is made to penetrate through the tissue around the perforation 42 to mount the suture instrument 16, and the perforation 42 is sutured by using this suture instrument 16. Accordingly, it is possible to suture the perforation 42 after respectively checking from the inside (the side from which the needle 14 is thrust) and the outside (the side through which the needle 14 penetrates or at which the anchor 27 is placed) of the stomach 43 that another tissue does not exist around the perforation 42. According to a suturing method using an endoscope of the prior art, it is impossible to check the opposite side. According to the endoscopic suturing method in this embodiment, it is possible to easily and certainly check for the existence of other tissues, as a result of which manipulation can be carried out with rapidity.

Modified examples of this embodiment are shown in FIGS. 17 to 22.

Figure 17:
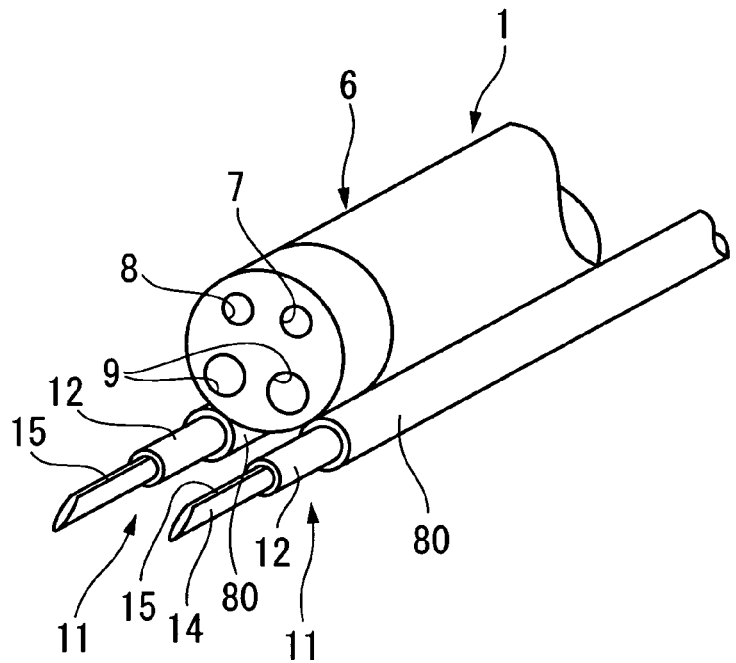
FIG. 17 is a schematic view showing one example of combination of an endoscope with a suture unit.
Figure 18:
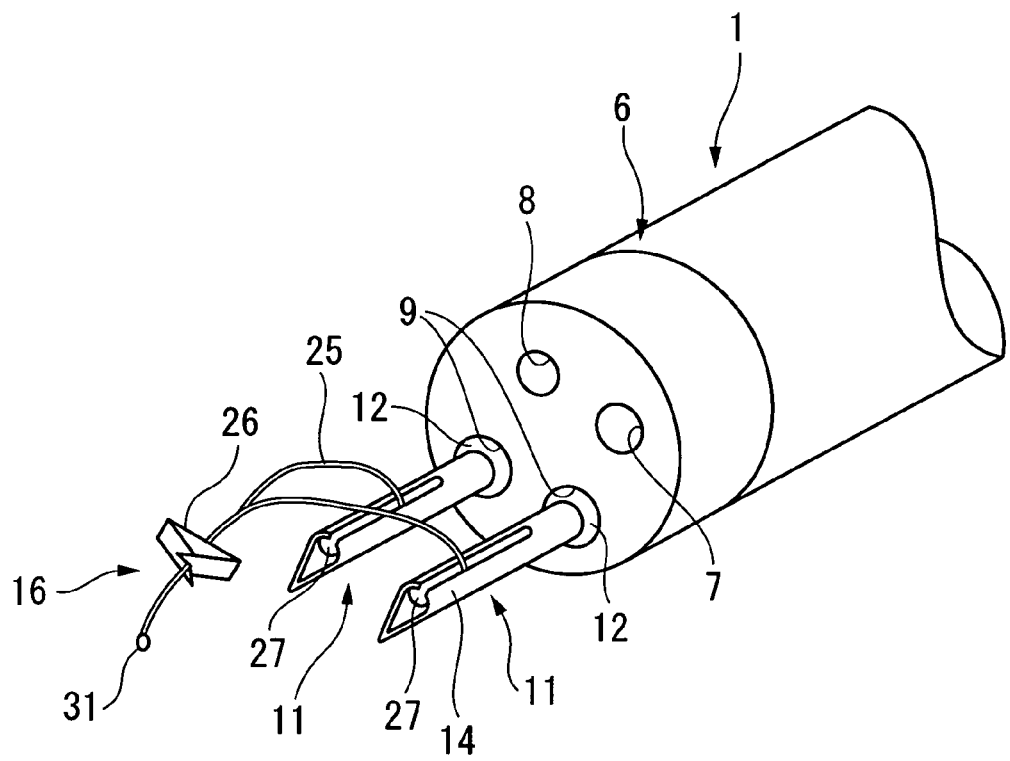
FIG. 18 is a schematic view showing one example of combination of an endoscope with a suture unit.

As shown in FIG. 17, two external sheaths 80 are provided at the periphery of the endoscope insertion part 6. A suture unit 11 is passed through each external sheath 80 so as to freely move forward or backward. The anchors 27 are individually contained in the respective needles 14. It is possible to thrust two needles 14 into the tissue at the same time or in an arbitrary order. As another example, one external sheath 80 may be used, and two anchors 27 may be contained in one needle 14. Moreover, FIG. 18 shows an example in which the suture units 11 are individually passed through two channels 9 of the endoscope insertion part 6.

Figure 19:
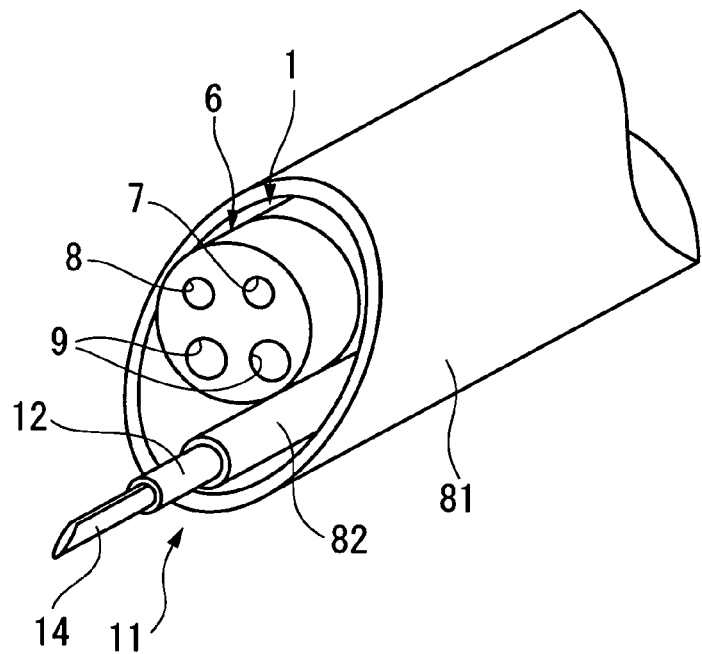
FIG. 19 is a schematic view showing one example of combination of an endoscope using an overtube with a suture unit.

As shown in FIG. 19, the endoscope insertion part 6 is inserted into an overtube 81. At the inner periphery of the overtube 81, a lumen 82 is provided, and the suture unit 11 is passed through the lumen 82. At the inner periphery of the overtube 81, two lumens 82 may be provided, and the suture units 11 may be individually passed through each of the lumens 82.

Figure 20:
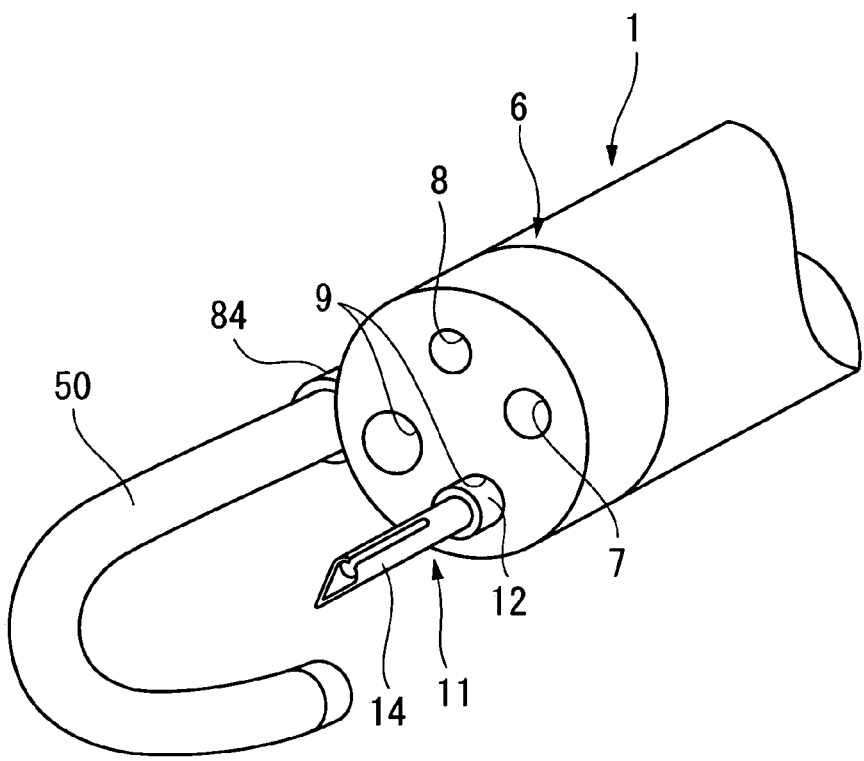
FIG. 20 is a schematic view showing one example of combination of an endoscope with an observation device.

As shown in FIG. 20, a channel 84 may be provided at the periphery of the endoscope insertion part 6, and the observation device 50 may be passed through this channel 84. Moreover, the observation device 50 may be directly provided at the periphery of the endoscope insertion part 6 without using the channel 84.

Figure 21:
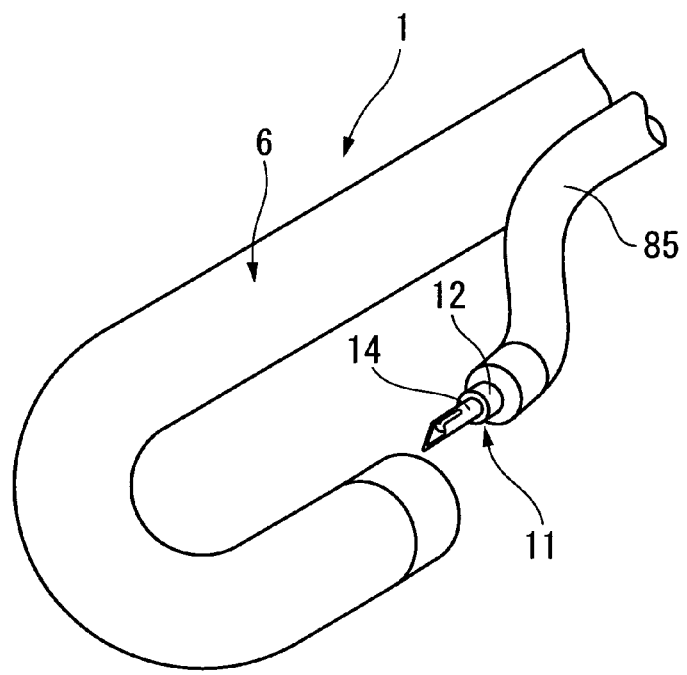
FIG. 21 is a schematic view showing one example of combination of an endoscope with a suture unit.

As shown in FIG. 21, an external channel 85 may be provided parallel to the endoscope insertion part 6, and the suture unit 11 may be passed through the channel 85. The tip portion of this channel 85 can be bent. When observing the perforation 42 from the abdominal cavity 44 side as shown in FIG. 6, the endoscope insertion part 6 is passed through the perforation 42 and moved into the abdominal cavity 44, and the tip portion of the endoscope insertion part 6 is then bent to observe by the observation device 7 provided at the tip portion thereof.

Figure 22:
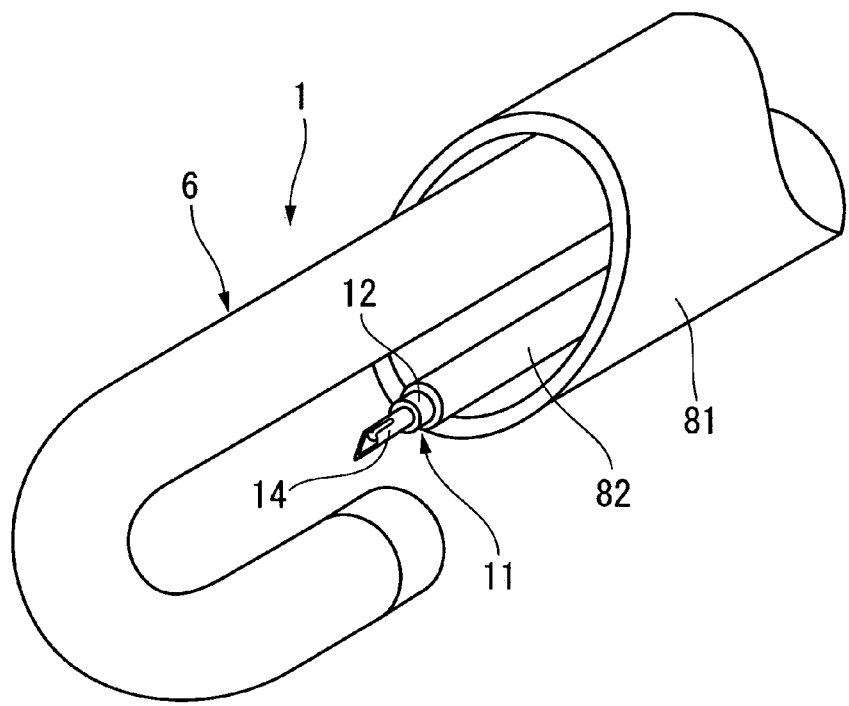
FIG. 22 is a schematic view showing one example of combination of an endoscope using an overtube with a suture unit.

As shown in FIG. 22, the suture unit 11 may be passed through the lumen 82 formed inside of the overtube 81. In this case, the area around the perforation 42 is observed from the abdominal cavity 44 side by using the observation device 7 of the endoscope insertion part 6.

Second Embodiment

In this embodiment, the same endoscope 1 and suture unit 11 as in the first embodiment are used. Descriptions that overlap with the first embodiment will be omitted.

Figure 23:
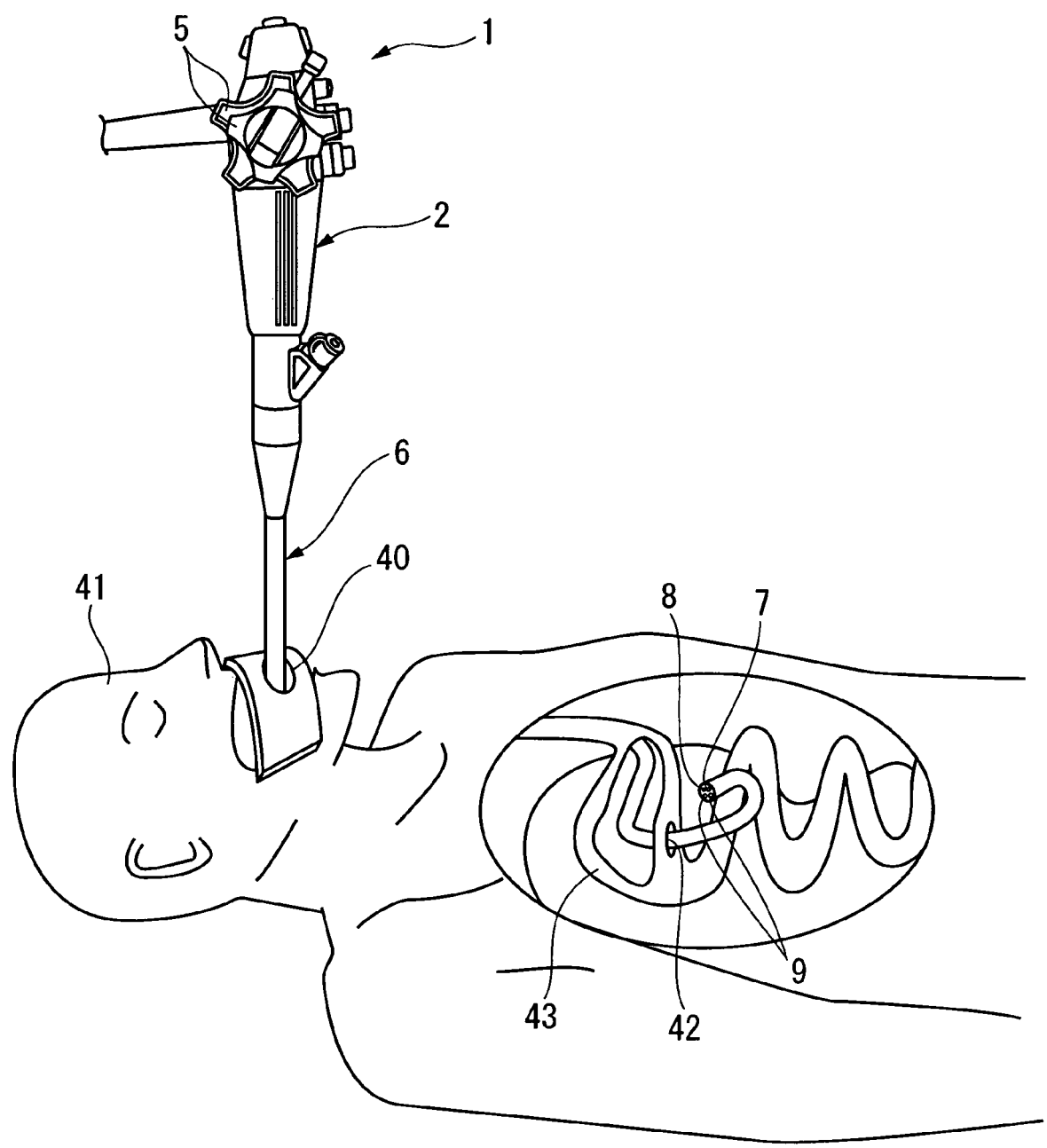
FIG. 23 is a schematic view showing a step of observing the outside of the stomach.
Figure 24:
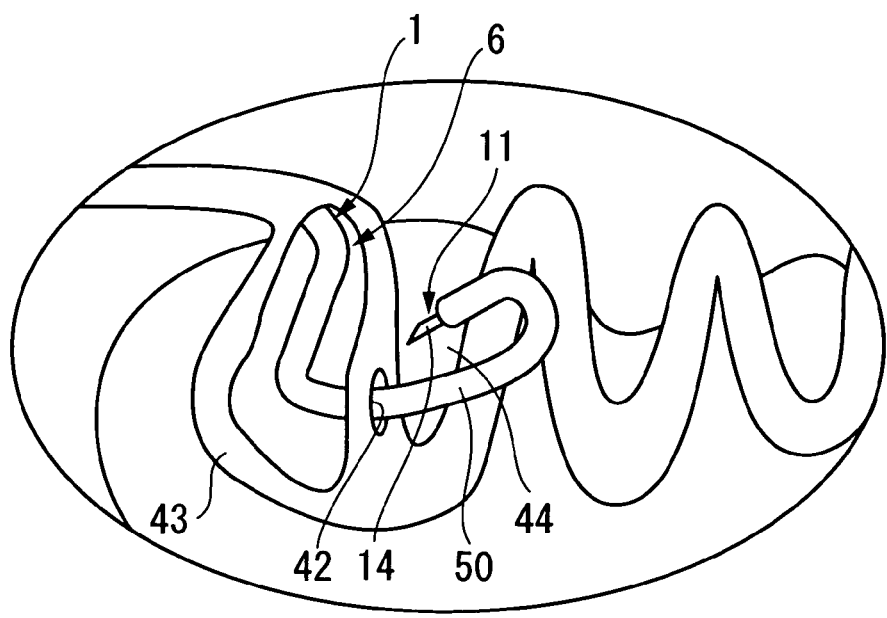
FIG. 24 is a schematic view showing a step of puncturing the tissue from the outside of the stomach with a needle of a suture unit.

A suturing method of this embodiment will be explained. As shown in FIG. 5, the endoscope insertion part 6 is inserted into the vicinity of the perforation 42 to observe the perforation 42 from the inside of the stomach 43. Next, as shown in FIG. 23, the endoscope insertion part 6 is moved from the perforation 42 into the abdominal cavity 44, and an area around the perforation 42 is then observed from the abdominal cavity 44 side by the observation device (first observation device) 7 of the endoscope insertion part 6. After confirming that other hollow organs do not exist in the area around the perforation 42, the needle 14 of the suture unit 11 is projected from the endoscope insertion part 6 as shown in FIG. 24, and the needle 14 is thrust from the abdominal cavity 44 side into the stomach 43. Since the safety of the inside of the stomach 43 is confirmed first, the inside of the stomach 43 may not be checked when thrusting the needle 14. The inside of the stomach 43, however, may be punctured while observing the inside of the stomach 43 (the side at which the anchor 27 is placed) by using another observation device. In this case, it is possible to puncture at the puncture position while observing both the inside and the abdominal cavity 44 side of the stomach 43.

Figure 25:
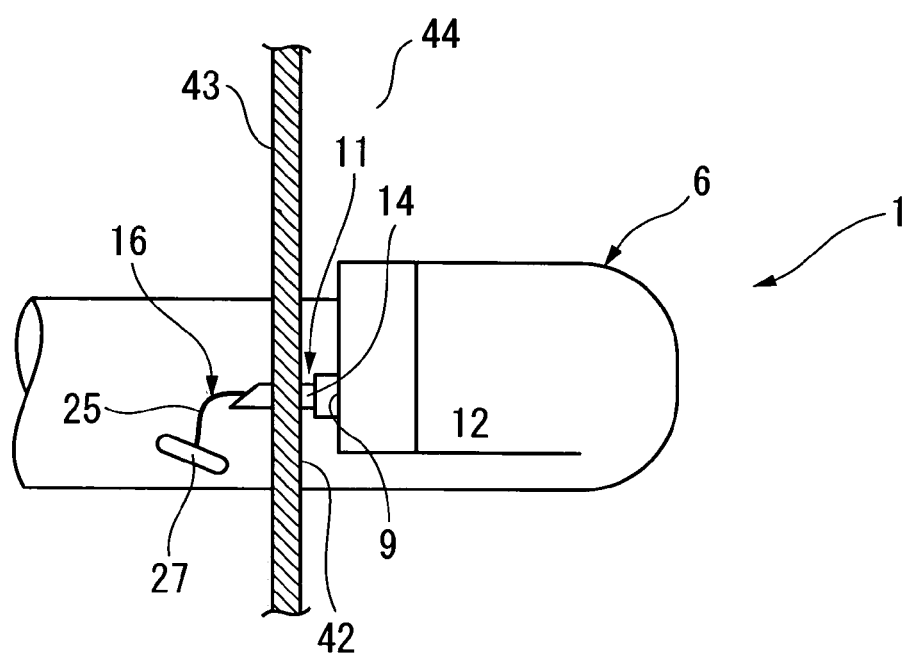
FIG. 25 is a schematic view showing a step of pushing out an anchor from a needle to the inside of the stomach.
Figure 26:
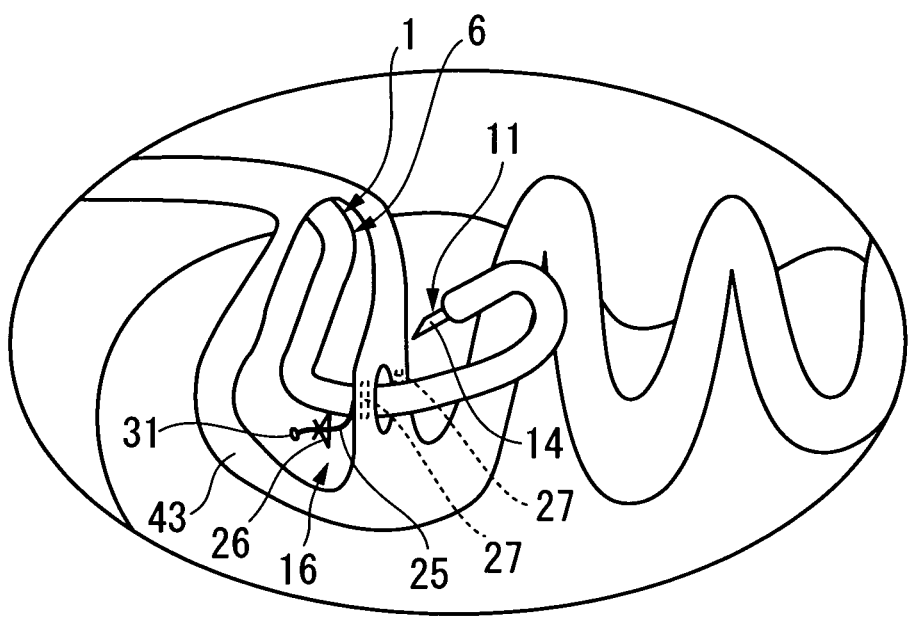
FIG. 26 is a schematic view in which two anchors are placed on the inside of the stomach.

As shown in FIG. 25, the first anchor 27 is extruded into the stomach 43 from the tip of the needle 14. As shown in FIG. 26, after placing two anchors 27 so as to sandwich the perforation 42 therebetween, the suture unit 11 is contained inside of the channel 9. After that, the endoscope 1 is drawn back to the inside of the stomach 43.

Figure 27:
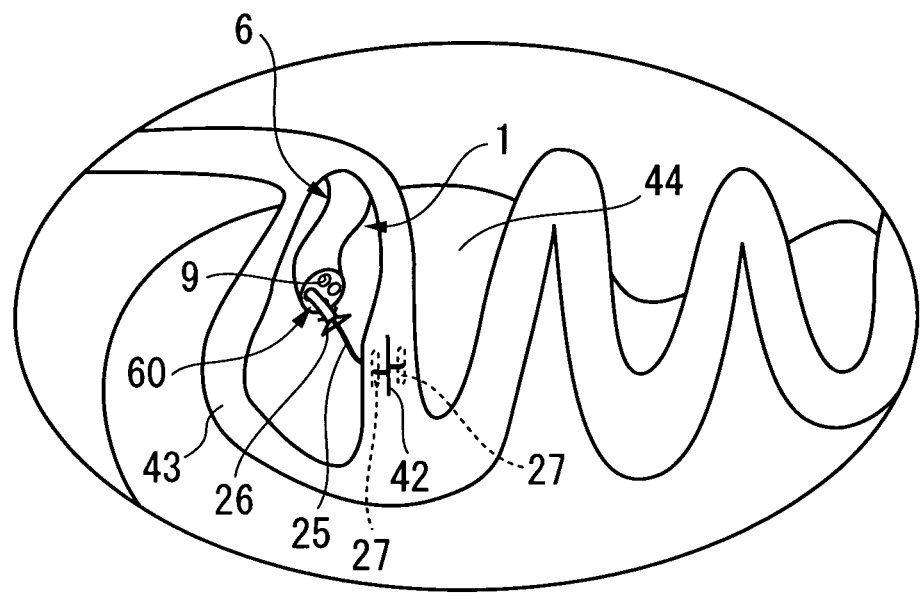
FIG. 27 is a schematic view showing a step of tightening up a perforation with a suture instrument.
Figure 28:
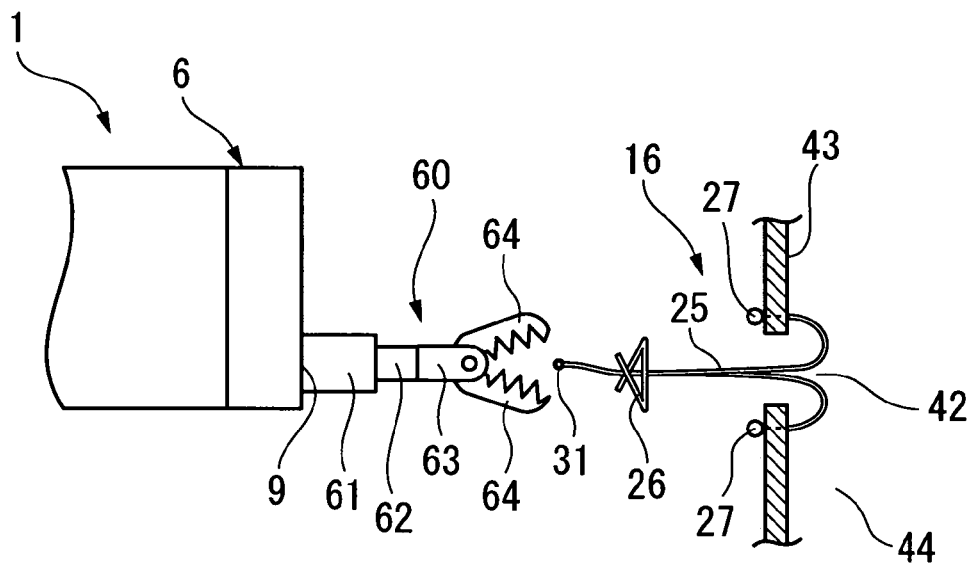
FIG. 28 is a schematic view showing manipulation for grasping a suture instrument by a forceps.
Figure 29:
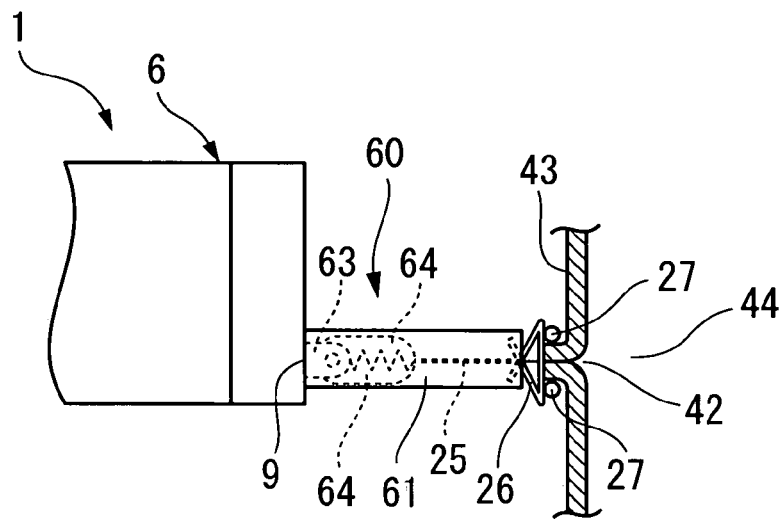
FIG. 29 is a view in which a perforation is sutured by a forceps and a suture instrument.

As shown in FIGS. 27 and 28, the forceps 60 is passed through the channel 9 of the endoscope 1 drawn back to the inside of the stomach 43. The forceps 60 grasps the knot 31 of the suture thread 25 existing in the abdominal cavity 44 side, and draws the suture thread 25 and the stopper 26 into the stomach 43 through the perforation 42. As shown in FIG. 29, when the stopper 26 is pressed against the tissue by the outer sheath 61, the suture instrument 16 tightens up the tissue, and thereby the perforation 42 is sutured.

In this embodiment, after observation of the inside of the stomach 43 by using the endoscope 1, the endoscope 1 is moved to the outside of the stomach 43 to check from the abdominal cavity 44 side that other tissues do not exist in the area around the perforation 42. After that, the needle 14 is thrust into the tissue from the outside to mount the suture instrument 16 and suture the perforation 42 while passing the endoscope 1 through the perforation 42. Accordingly, other tissues can be easily prevented from being sutured together when suturing by using the endoscope 1.

Third Embodiment

In this embodiment, the same endoscope 1 and suture unit 11 as in the first embodiment are used. Descriptions that overlap with the first embodiment will be omitted.

Figure 30:
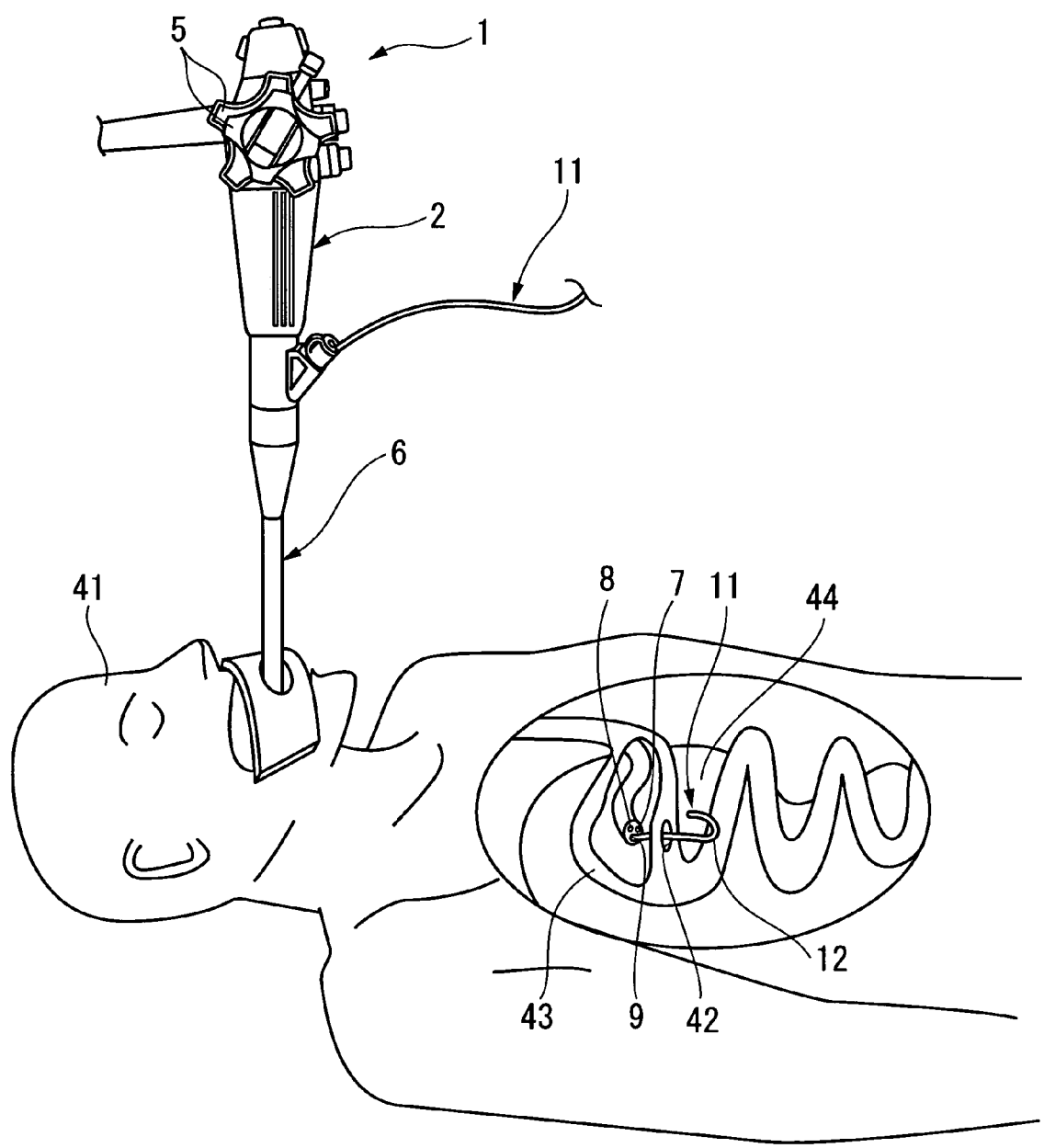
FIG. 30 is a schematic view showing a step of observing the outside of the stomach.

A suturing method of this embodiment will be explained. As shown in FIG. 5, the endoscope insertion part 6 is inserted in the vicinity of the perforation 42 to observe the perforation 42 from the inside of the stomach 43. Next, as shown in FIG. 23, the endoscope insertion part 6 is moved from the perforation 42 into the abdominal cavity 44, and an area around the perforation 42 is then observed from the abdominal cavity 44 side by the observation device (first observation device) 7 of the endoscope insertion part 6. After checking that other tissues do not exist in the area around the perforation 42 (the position through which the needle 14 is passed, the puncture position, or the position at which the anchor 27 is placed), the endoscope insertion part 6 is drawn back to the inside of the stomach 43. Next, the suture unit 11 which is passed through the channel 9 is projected. As shown in FIG. 30, the tip portion of the suture unit 11 is moved from the perforation 42 to the abdominal cavity 44. The tip portion of the suture unit 11 is then bent to face the outside of the stomach 43 and an area around the perforation 42 in the abdominal cavity 44.

Figure 31:
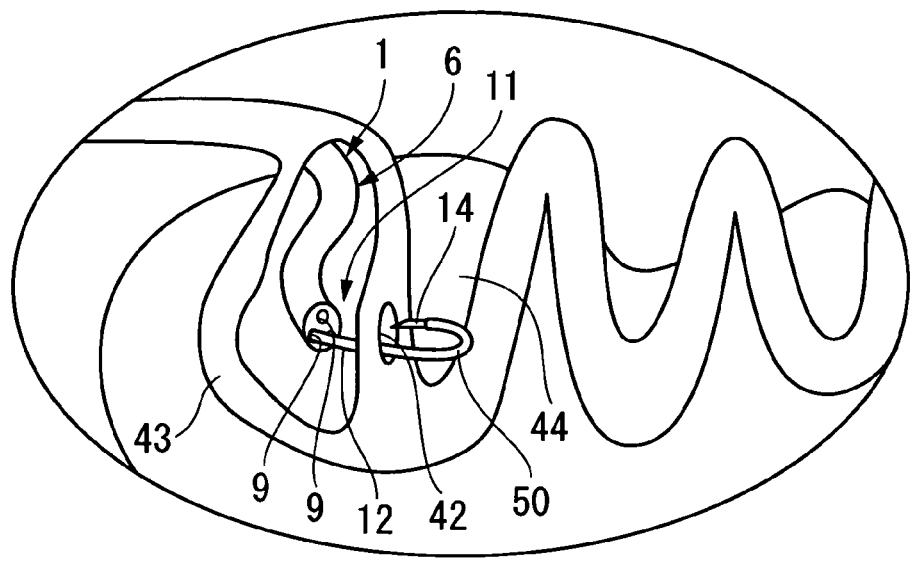
FIG. 31 is a schematic view showing a step of puncturing the tissue with a needle of a suture unit.
Figure 32:
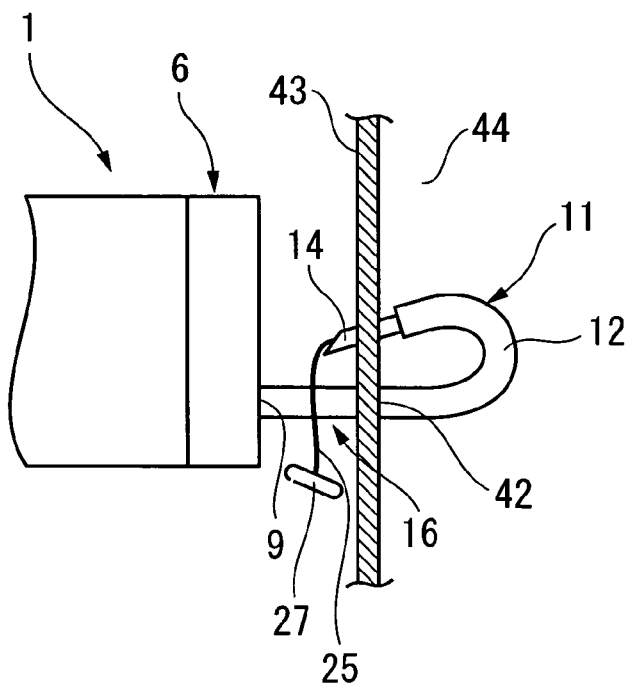
FIG. 32 is a schematic view showing a step of pushing out an anchor from a needle to the inside of the stomach.
Figure 33:
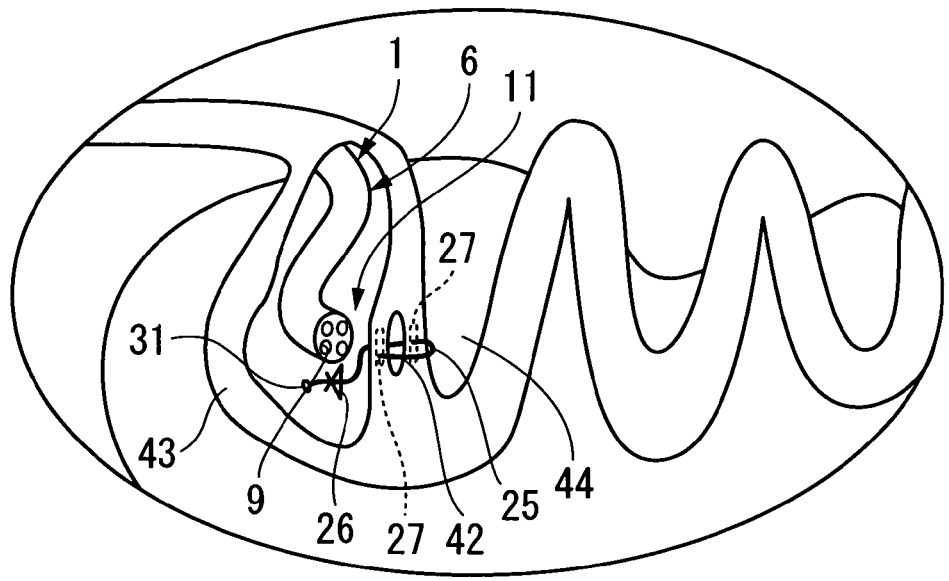
FIG. 33 is a schematic view in which two anchors are placed on the inside of the stomach.
Figure 34:
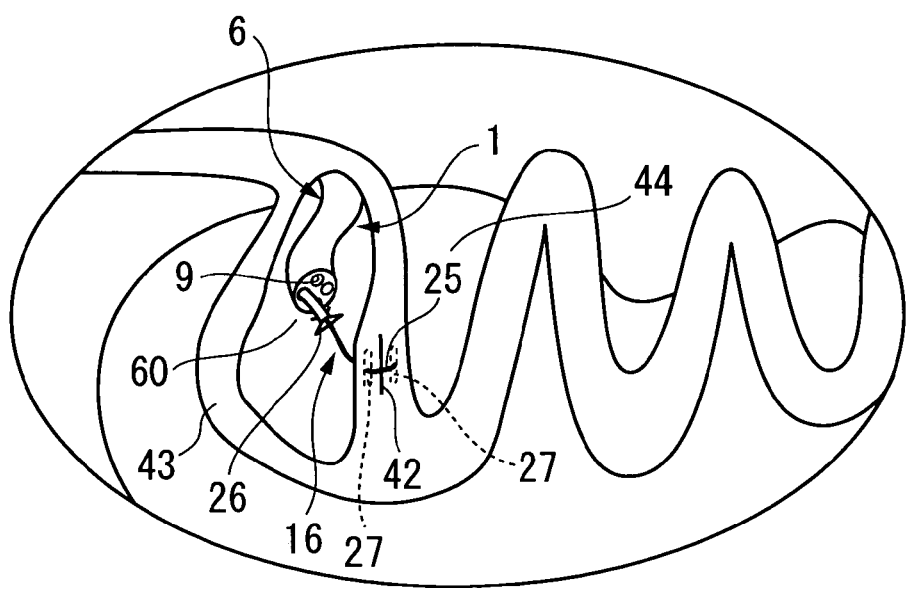
FIG. 34 is a schematic view showing a step of tightening up a perforation with a suture instrument.

As shown in FIG. 31, the suture unit 11 projects the needle 14 from the outer sheath 12, and the needle 14 penetrates the tissue around the perforation 42 from the abdominal cavity 44 side into the stomach 43. It is preferable that the stopper 26 be made to enter the stomach 43 when the needle 14 is projected from the outer sheath 12. As shown in FIG. 32, after the needle 14 penetrates the tissue, the first anchor 27 is pushed out and placed inside of the stomach 43. As shown in FIG. 33, after placement of two anchors 27 inside the stomach 43 so as to sandwich the perforation 42 therebetween, the suture unit 11 is drawn back to the inside of the stomach 43, and contained in the channel 9. As shown in FIG. 34, the forceps 60 is then passed through the channel 9, and the tissue is tightened up by the suture instrument 16 using the forceps 60 to suture the perforation 42. The suturing method is the same as in the second embodiment.

In this embodiment, after the inside and the outside of the stomach 43 are sequentially observed by the observation device 7 of the endoscope 1 to check that other tissues do not exist in an area around the perforation 42, the endoscope 1 is drawn back to the inside of the stomach 43, and the tissue is punctured with the needle 14 from the outside of the stomach 43. Accordingly, other tissues can be easily prevented from being sutured together when suturing by using the endoscope 1.

Figure 11:
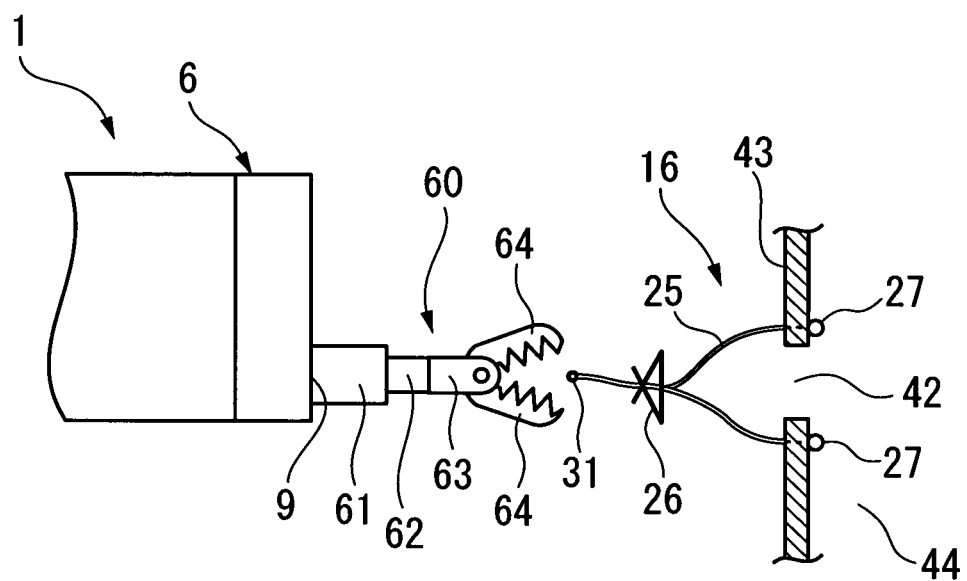
FIG. 11 is a schematic view showing manipulation for grasping a suture instrument gripped by a forceps.
Figure 35:
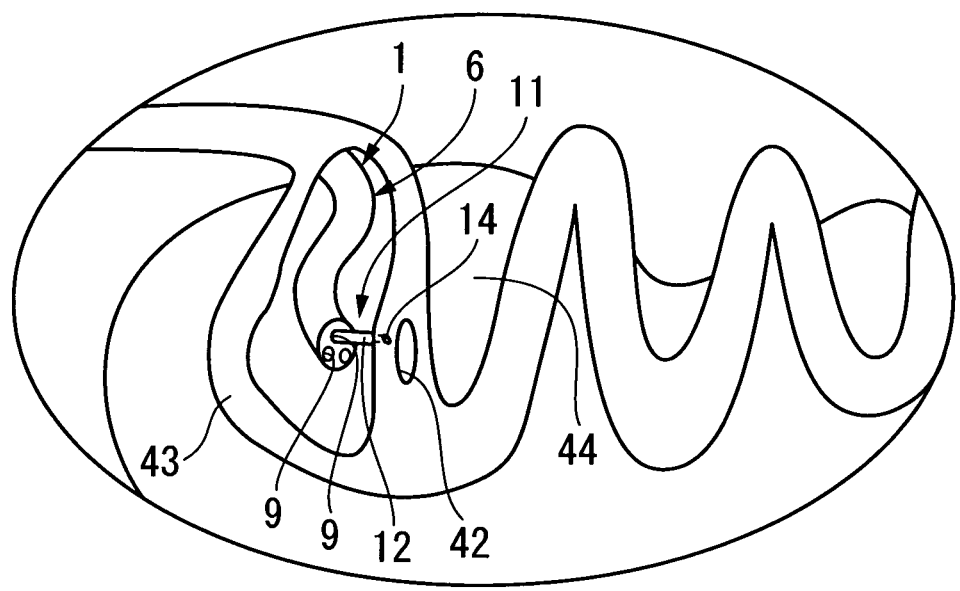
FIG. 35 is a schematic view showing a step of thrusting a needle from the inside of the stomach after observing the inside and the outside of the stomach by an endoscope.

Next, modified examples of this embodiment will be explained. As shown in FIG. 23, after observing the outside of the stomach 43 by using the observation device 7 of the endoscope insertion part 6, the endoscope insertion part 6 is drawn back to the inside of the stomach 43. After that, the suture unit 11 is projected from the endoscope insertion part 6 present in the stomach 43, and the needle 14 is thrust from the inside into the outside of the stomach 43, as shown in FIG. 35. After placement of the anchor 27 at the outside of the stomach 43, the suture instrument 16 is tightened up to suture the perforation 42, as shown in FIGS. 11 and 12. In this case, other tissues can be easily prevented from being sutured together when suturing by using the endoscope 1.

Figure 36:
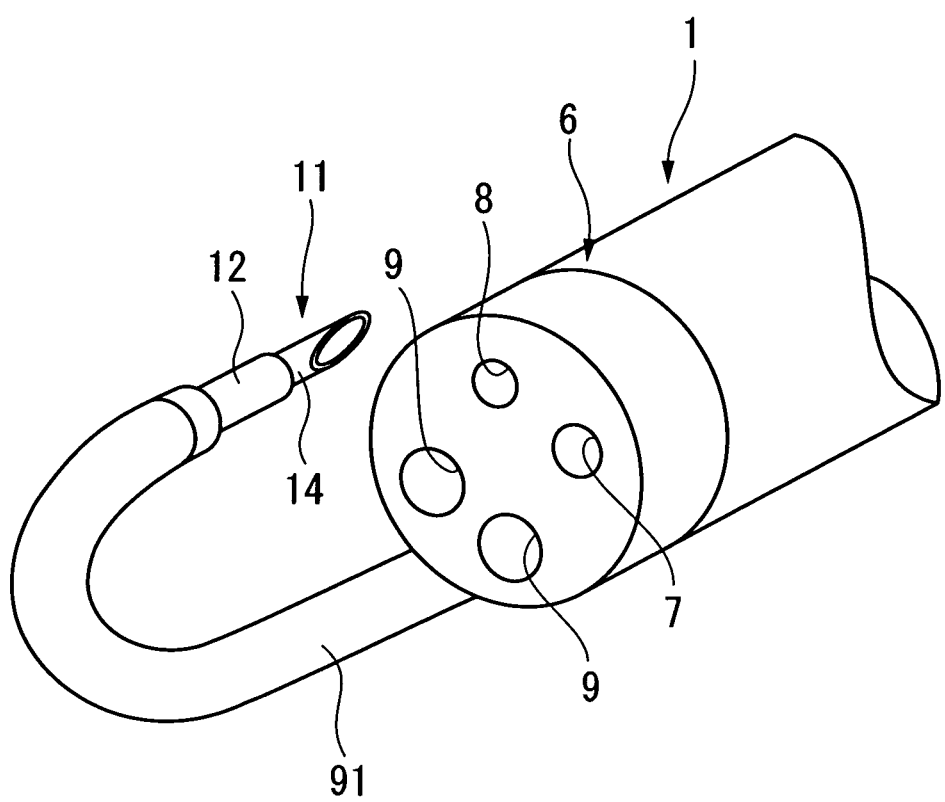
FIG. 36 is a schematic view showing one example of combination of an endoscope with a suture unit.

As shown in FIG. 36, a channel 91 may be provided at the periphery of the endoscope insertion part 6, and the suture unit 11 may be passed through this channel 91. Moreover, the suture unit 11 may be provided parallel to the periphery of the endoscope insertion part 6. The tip portion of the suture unit 11 is constructed so as to be able to be independently bent.

This invention can be widely applied without being limited to the above-mentioned embodiments.

For example, the endoscope 1 may be inserted from the anus into the colon which is an example of a hollow organ. In this case, a perforation formed in the colon is sutured. Although the perforation 42 is described as being already formed, the manipulation of the above-mentioned embodiment may be carried out after forming the perforation 42 by using the endoscope 1. In this case, the endoscope 1 is inserted from a natural opening into the inside of the stomach 43, and a determined incision portion is checked by the observation device 7 provided at the tip of the endoscope insertion part 6. After that, the determined incision portion is incised after passing a high-frequency knife or the like through the channel 9 of the endoscope 1 to form the perforation 42.

Figure 37:
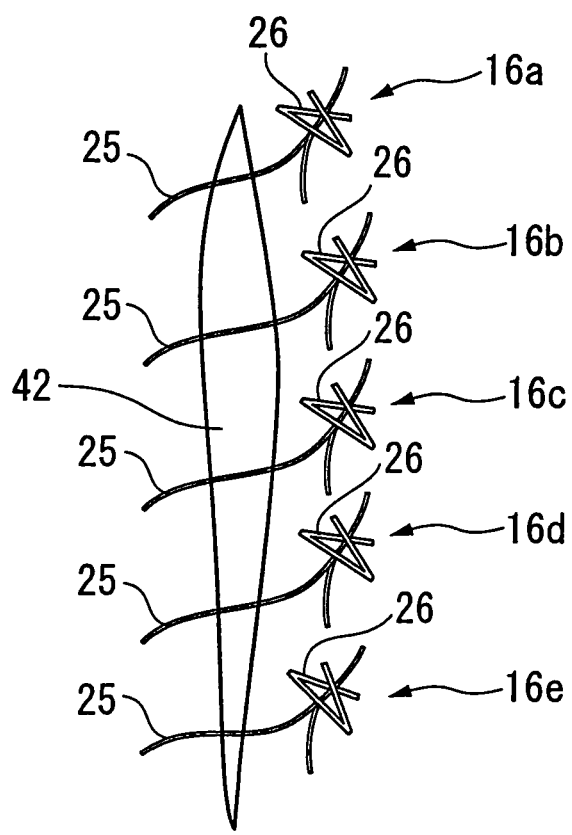
FIG. 37 is a view showing the order for tightening up plural suture instruments.

When the stomach 43 is widely incised and the perforation 42 is sutured by using at least three suture instruments 16, suture instruments 16 plurally lined up are preferably sequentially tightened up from one end thereof. In an example shown in FIG. 35, a suture instrument 16a, a suture instrument 16b, a suture instrument 16c, a suture instrument 16d, and a suture instrument 16e are tightened up in this order, for example. Since the perforation 42 is sutured from one end thereof, and the size of the perforation 42 can be gradually diminished, suturing can be easily carried out. Alternatively, the suture instrument 16 at the center of the suture instruments 16 lined up may be tightened up first, followed by tightening the suture instruments 16 at the center positions between the suture instrument 16 tightened up at the center position and the suture instruments 16 at the ends thereof. In the example shown in FIG. 37, the suture instrument 16c is tightened up first, the suture instrument 16b and the suture instrument 16d are then tightened up, and the suture instrument 16a and the suture instrument 16e are finally tightened up. Since the center position of the opening is always sutured, the degree of slippage of suture positions can be diminished.

What is claimed is:

1. A method for suturing a perforation, comprising the steps of:

inserting a first observation device which is provided on a distal end of an endoscope having at least two channels including a first channel and a second channel from a natural opening of a living body into a hollow organ;

inserting a second observation device which is inserted in the first channel and is retained therein into the hollow organ accompanying the insertion of the endoscope;

inserting a tip of the second observation device through the perforation into a body cavity by making the tip of the second observation device protrude from the distal end of the endoscope through the first channel;

observing a puncture position from an inside of the hollow organ by the first observation device and from a body cavity side of the hollow organ by bending the inserted tip of the second observation device to face the puncture position;

inserting a needle of a suture unit from the natural opening into the hollow organ by inserting the needle through the second channel provided in the endoscope;

thrusting the needle into a tissue around the perforation to make a suture thread puncture the tissue via the needle;

drawing the second observation device back to the inside of the hollow organ; and closing the perforation by tightening up the suture thread puncturing the tissue, wherein the puncture position is a position through which the needle passes.

2. The method according to claim 1, wherein the needle is thrust from the inside to the body cavity side of the hollow organ while observing the hollow organ from the body cavity side by the second observation device.

3. The method according to claim 1, further comprising a step of moving aside a tissue which interferes at the puncture position.

4. The method according to claim 1, wherein the step of thrusting the needle comprises:

inserting a tip portion of the suture unit into the body cavity through the perforation;

bending the inserted tip portion to face the puncture position; and thrusting the needle into the puncture position from the body cavity.

5. The method according to claim 3, wherein in the step of moving aside the tissue, a retracting instrument is inserted to form a space through which the needle is passed.

6. The method according to claim 1, wherein the step of thrusting the needle further comprises observing a tip of the needle from the body cavity side by the second observation device.

7. The method according to claim 1, wherein in the step of thrusting the needle, the suture thread is made to puncture the tissue while observing from both the inside and the body cavity side using the first observation device and the second observation device.

* * * * *